(12) United States Patent  (10) Patent No.: US 7,806,895 B2
Weier et al.  (45) Date of Patent: Oct. 5, 2010

(54) THORACIC CLOSURE DEVICE AND METHODS

(75) Inventors: Christopher Weier, Baltimore, MD (US); Neha Malhotra, Baltimore, MD (US); Alexander King, Baltimore, MD (US)

(73) Assignee: Device Evolutions LLC, Princeton, NJ (US)

( * ) Notice: Subject to any disclaimer, the term of this patent is extended or adjusted under 35 U.S.C. 154(b) by 596 days.

(21) Appl. No.: 11/745,314

(22) Filed: May 7, 2007

(65) Prior Publication Data

US 2007/0260251 A1  Nov. 8, 2007

Related U.S. Application Data

(60) Provisional application No. 60/798,978, filed on May 8, 2006.

(51) Int. Cl.
  *A61B 17/82* (2006.01)
(52) U.S. Cl. .............. 606/74; 81/9.3; 81/337; 140/93 A; 140/93.2; 254/199; 254/245; 254/246; 254/248; 606/103; 606/113; 606/139; 606/151
(58) Field of Classification Search .......... 606/74, 606/103, 113, 139, 151; 81/9.3, 337; 140/93 A, 140/93.2; 254/199, 245, 246, 248
  See application file for complete search history.

(56) References Cited

U.S. PATENT DOCUMENTS

| | | | |
|---|---|---|---|
| 3,645,302 A * | 2/1972 | Caveney et al. | 140/93.2 |
| 3,661,187 A * | 5/1972 | Caveney et al. | 140/123.6 |
| 4,535,764 A * | 8/1985 | Ebert | 606/74 |
| 4,688,302 A * | 8/1987 | Caveney et al. | 24/16 PB |
| 4,730,615 A * | 3/1988 | Sutherland et al. | 606/215 |
| D309,350 S | 7/1990 | Sutherland | |
| 5,219,358 A * | 6/1993 | Bendel et al. | 606/222 |
| 5,339,870 A | 8/1994 | Green | |
| 5,355,913 A | 10/1994 | Green | |
| 5,366,461 A * | 11/1994 | Blasnik | 606/151 |
| 5,383,882 A * | 1/1995 | Buess et al. | 606/157 |
| 5,395,374 A * | 3/1995 | Miller et al. | 606/74 |
| 5,462,542 A | 10/1995 | Alesi | |
| 5,549,619 A | 8/1996 | Peters | |
| 5,766,218 A * | 6/1998 | Arnott | 606/151 |
| 6,050,998 A | 4/2000 | Fletcher | |
| 6,120,436 A | 9/2000 | Anderson | |
| 6,146,386 A | 11/2000 | Blackman | |
| 6,200,318 B1 * | 3/2001 | Har-Shai et al. | 606/74 |
| 6,217,580 B1 | 4/2001 | Levin | |
| 6,302,889 B1 | 10/2001 | Keller | |
| 6,530,929 B1 * | 3/2003 | Justis et al. | 606/103 |
| 6,589,246 B1 | 7/2003 | Hack | |
| 6,872,210 B2 | 3/2005 | Hearn | |
| 6,969,391 B1 | 11/2005 | Gazzani | |
| 7,008,429 B2 | 3/2006 | Golobek | |
| 2002/0045904 A1 * | 4/2002 | Fuss et al. | 606/99 |
| 2005/0240189 A1 | 10/2005 | Rousseau | |

* cited by examiner

*Primary Examiner*—Thomas C Barrett
*Assistant Examiner*—Christian Sevilla
(74) *Attorney, Agent, or Firm*—PatentBest; Andrew McAleavey

(57) ABSTRACT

A thoracic closure device. The device has a handle member, a base member, and a feed path, and is designed to accept and, with a ratcheting mechanism, tension a toothed closure tie. A guide member is also provided, and assists in the placement of a closure tie prior to tensioning. Methods of closing a median sternotomy using toothed closure ties are also disclosed.

19 Claims, 4 Drawing Sheets

THORACIC CLOSURE DEVICE AND METHODS

CROSS-REFERENCE TO RELATED APPLICATIONS

This application claims priority to U.S. Provisional Patent Application No. 60/798,978, filed May 8, 2006, the contents of which are incorporated by reference herein in their entirety.

BACKGROUND OF THE INVENTION

1. Field of the Invention

The invention relates to surgical devices and methods and, specifically, to devices and methods for closing the chest.

2. Description of Related Art

A median sternotomy is a surgical procedure in which a vertical incision is made along the midline of the sternum and the sternum is divided. Median sternotomies provide access for thoracic surgical procedures, including coronary artery bypass and heart transplant. In 2002, 709,000 median sternotomies were performed in the United States.

When the surgical procedure that necessitated the median sternotomy is complete, the sternum is closed. Typically, needles are used to loop wire through the manubrium, the bone that defines the top of the sternum. Below the manubrium, wires are looped through the intercostal spaces and around the sternum. The loops of wire are cut to create individual lengths of wire, and the ends of those lengths of wire are twisted together to tension them.

Certain difficulties arise with the traditional manner of closing a median sternotomy. First, it can be difficult for the surgeon to estimate the necessary amount of closure force correctly. Additionally, threading the wire around and through the sternum creates an increased risk of organ puncture. Moreover, after the procedure is performed, other difficulties may arise. For example, the patient may have a foreign body reaction, and the presence of metal wires may preclude or restrict the use of certain imaging techniques, like magnetic resonance imaging (MRI). Ultimately 3-5% of patients may require a re-sternotomy due to inadequate closure or complications.

SUMMARY OF THE INVENTION

One aspect of the invention relates to a thoracic closure device that is constructed and adapted to place toothed closure ties during a surgical procedure and to tension those ties to bring together two parts of a bone or other structure. The thoracic closure device may be used, for example, in the closure of a median sternotomy. The device itself has a guide member that may be pivoted from a stored position in the device handle to aid in the placement of a closure tie. Once the closure tie has been secured around the bone, the device can be used to apply a unidirectional ratcheting tightening force to the closure tie.

Other aspects, features, and advantages of the invention will be set forth in the description that follows.

BRIEF DESCRIPTION OF THE DRAWINGS

The invention will be described with respect to the following drawing figures, in which like numerals represent like features throughout the drawings, and in which.

DETAILED DESCRIPTION

Figure 1:
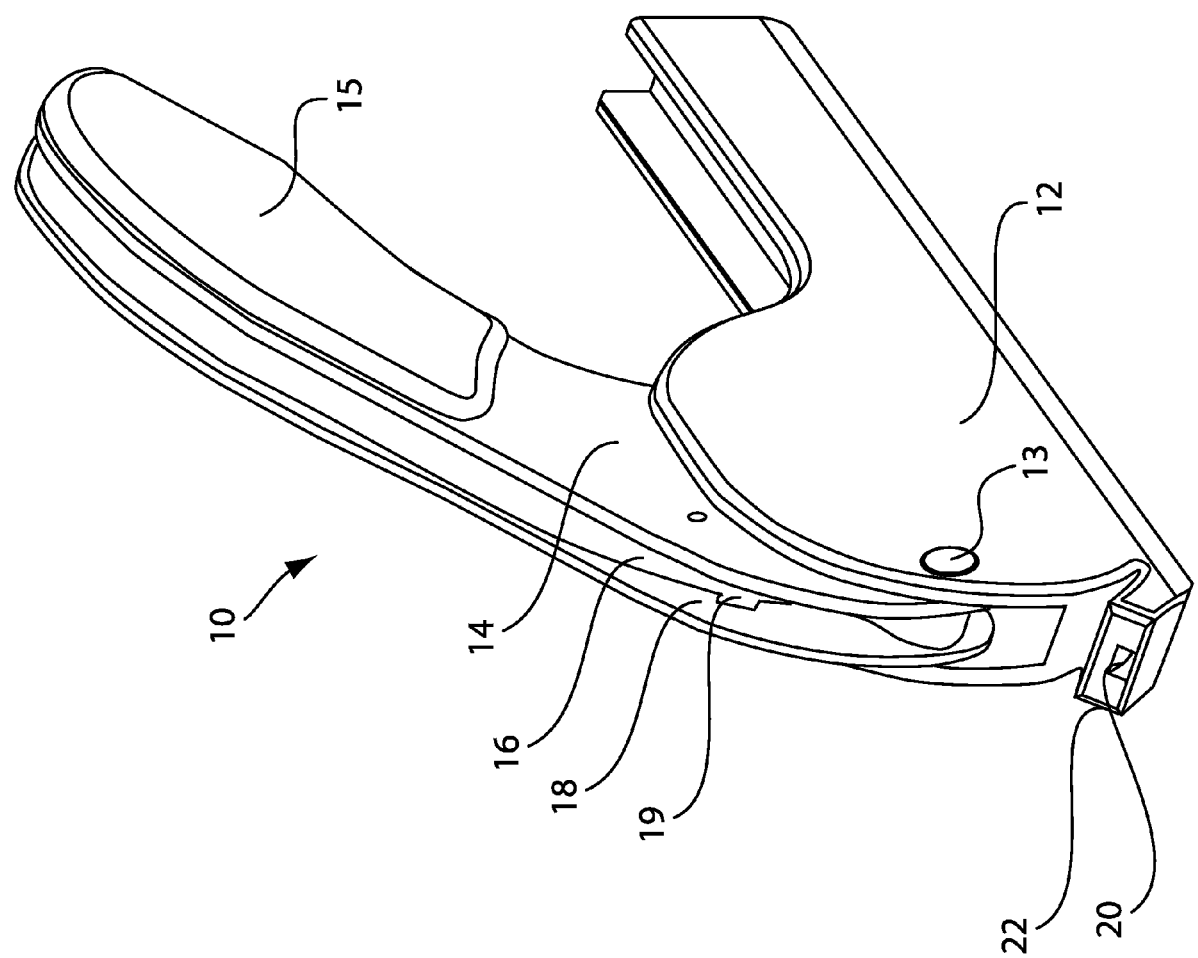
FIG. 1 is a perspective view of a thoracic closure apparatus according to one embodiment of the invention.

FIG. 1 is a perspective view of a thoracic closure device, generally indicated at 10, according to one embodiment of the invention. The thoracic closure device 10 has a base member 12 and a handle member 14 mounted on the base member 12 for rotation about a generally horizontally-extending axis of rotation. In the illustrated embodiment, the handle member 14 includes grip structures 15 on its sides to make it easier to grip and hold. A guide member 16 is mounted for rotation on a fixed pivot 13 in a recess 18 in the top surface of the handle member 14. When in a fully retracted position, the guide member 16 is substantially within the recess 18.

Figure 2:
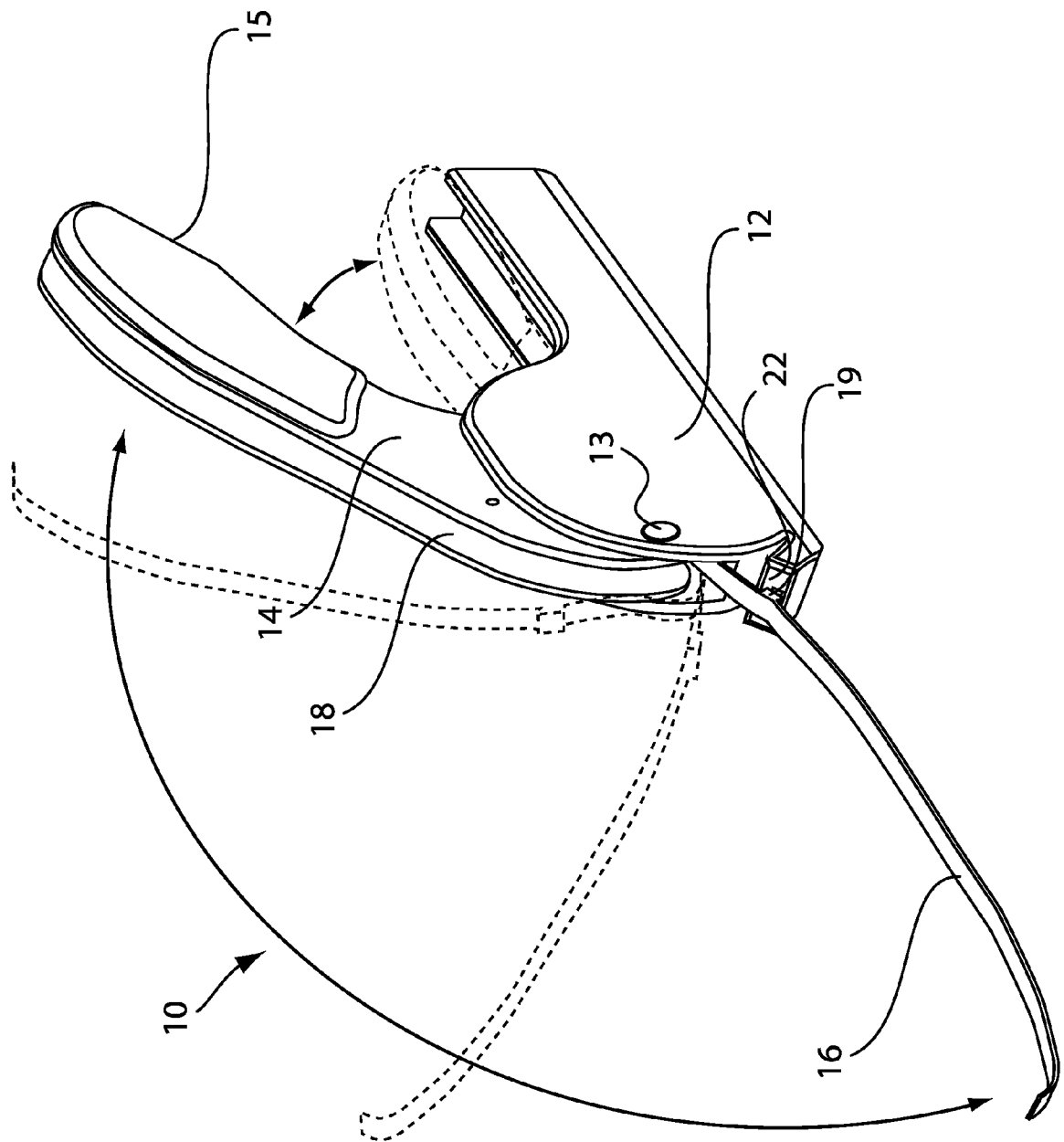
FIG. 2 is a perspective view of the thoracic closure apparatus of FIG. 1 with its guide member extended.

FIG. 2 is a perspective view of the device 10 with the guide member 16 rotated into an extended position in which it extends forwardly of the rest of the device 10. The guide member 16 is an elongate member, metal in the illustrated embodiment, which is generally "U"-shaped with an elongated trough. Overall, the guide member 16 has a length such that when the position illustrated in FIG. 1, it covers a substantial portion of the length of the handle member 14, and when in the position shown in FIG. 2, it extends significantly beyond the front of the device 10. The distal end of the guide member 16 may be at least slightly sharpened. Close to its rotationally mounted end, the guide member 16 includes a projecting block 19.

As will be described in greater detail below, the device 10 is constructed and arranged to assist in the placement and tensioning of a toothed, unidirectionally tensionable closure tie, also commonly referred to as a zip tie, in order to close a median sternotomy or another kind of break or tear in tissue that requires a tensioned closure. The guide member 16 assists with the placement of the closure tie by creating a path through surrounding tissues for the insertion of the closure tie; a ratcheting mechanism within the device 10 tensions the closure tie once it is placed.

At one end, the base member 12 includes a first opening 20, which, in the illustrated embodiment, is provided at the end of a short, slightly curvilinear projection 22. The position of the projection 22 is such that when the guide member 16 is in the position shown in FIG. 2, the projecting block 19 rests against the projection 22, and the projection 22 thus supports and buttresses the extended position of the guide member 16.

The first opening 20 is constructed, dimensioned, and arranged to accept an end portion of a closure tie, and defines one end of a feed path along which the closure tie is fed in order to tension it. Although the first opening 20 in the illustrated embodiment is at essentially the forwardmost end of the device 10, it should be understood that the ends of the feed path need not necessarily be provided at the physical ends of the device 10.

Figure 3:
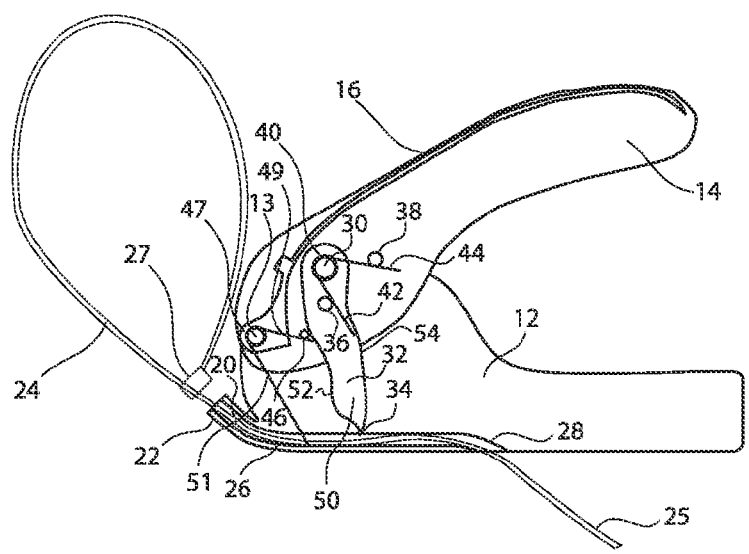
FIG. 3 is a schematic sectional side elevational view of the thoracic closure apparatus of FIG. 1 with its handle in a fully upward position.

FIG. 3 is a schematic sectional side elevational view of the device 10 with a closure tie 24 in the feed path and the handle member 14 in its fully upward position. In FIG. 3, the external details of the base member 12 and handle member 14 are simplified in order to show the relationships between the interior components.

As shown in FIG. 3, the tongue end 25 of the closure tie 24 extends into the first opening 20, and the other end 27 of the closure tie 24, the end with engaging structure, remains outside of the device 10 and may bear against the projection 22 as tension is applied to the closure tie 24. The feed path for the closure tie 24 in the illustrated embodiment of the device 10 extends from the first opening 20 along an interior surface 26 of the device 10, and terminates at a second opening 28 provided in the interior surface 26. In the device 10, the interior surface 26 comprises the bottom interior surface of the base member 12, and the closure tie 24 thus exits the base member 12, through an opening in its bottom surface, although that need not be the case in all embodiments.

The device 10 provides a mechanism such that when the handle member 14 is moved between the upward position illustrated in FIGS. 1-3 and a depressed position proximate to the base member 12 (shown in phantom in FIG. 2), the closure tie 24 is moved along the feed path. The handle member 14 includes an internal fixed pivot 30 that extends between its interior side surfaces and defines a generally horizontally-extending axis of rotation. Mounted for rotation on the fixed pivot 30 is a pawl arm 32.

The pawl arm 32 is constructed and arranged such that it extends from the fixed pivot 30 toward the interior surface 26, and is thus in a position to engage the interdental spaces of the toothed closure tie 24 when the handle member 14 is depressed. At its end, the pawl arm 32 includes a point 34 constructed and shaped to engage those interdental spaces. In the position shown in FIG. 3, because the handle member 14 is in its upwardmost position, the point 34 lies a very short distance from the teeth of the closure tie 24 and is not engaged with them.

The handle member 14 and pawl arm 32 are constructed and arranged such that the pawl arm 32 is driven by movement of the handle member 14; therefore, movement of the handle member 14 causes movement of the pawl arm 32. In order to cause the handle member 14 to drive movement of the pawl arm 32, the pawl arm 32 includes a pin 36 that projects from its lateral surface. Another pin 38 projects from an interior side surface of the handle member 14. An elastic member 40, which, in the illustrated embodiment, is a torsional spring, is mounted on the same fixed pivot 30 with one leg 42 bearing against the pin 36 on the pawl arm 32 and the other leg 44 bearing against the pin 38 projecting from the interior surface of the handle member 14.

The elastic member 40 does not rotate on the fixed pivot 30; instead, when the handle member 14 is moved, the legs 42, 44 of the elastic member 40, which rest on the pins 36, 38, are squeezed together, creating a resilient force. In general, the elastic member 40 biases the pawl arm 32 to rotate clockwise (with respect to the coordinate system of FIG. 3), toward the interior surface 26 and, thus, into engagement with a closure tie 24 in the feed path. The pins 36, 38 may include grooves or any other structure that is desirable or advantageous in retaining the legs 42, 44 of the elastic member 40.

A stop pin 46 extends from an interior side surface of the handle member 14, projects into the path of the pawl arm 32, and acts as a stop to prevent the pawl arm 32 from rotating too far toward the first opening 20, and to prevent it from contacting the closure tie 24 too early along the feed path. The action of the stop pin 46 can best be seen in FIG. 3, in which the pawl arm 32 is abutting it.

In addition to the elastic member 40, which causes the handle member 14 to drive the pawl arm 32, a second elastic member 47 is mounted on the same fixed pivot 13 on which the guide member 16 is mounted, in such a manner that the presence and action of the second elastic member 47 do not influence or obstruct the movement of the guide member 16. (For example, if the guide member 16 is mounted on the pivot 13 by two portions that are spaced from one another, the elastic member 47 may be mounted between those two portions.) The second elastic member 47, also a torsional spring in the illustrated embodiment, bears against the base member 12 and the handle member 14 and resiliently biases those two components apart. Like the elastic member 40, the second elastic member 47 is fixed in position. As shown, one leg 49 of the second elastic member 47 bears against the stop pin 46 in the handle member 14; the other leg 51 of the second elastic member 47 is longer, and bears against the bottom surface 26 of the base member 12 at a point that is to the side of the feed path and does not interfere with the action of the mechanism on a closure tie 24. As the handle member 14 is moved toward the base member 12, the legs 49, 51 are moved closer to one another, creating a resilient force that tends to return the handle member 14 to its upward position.

Figure 4:
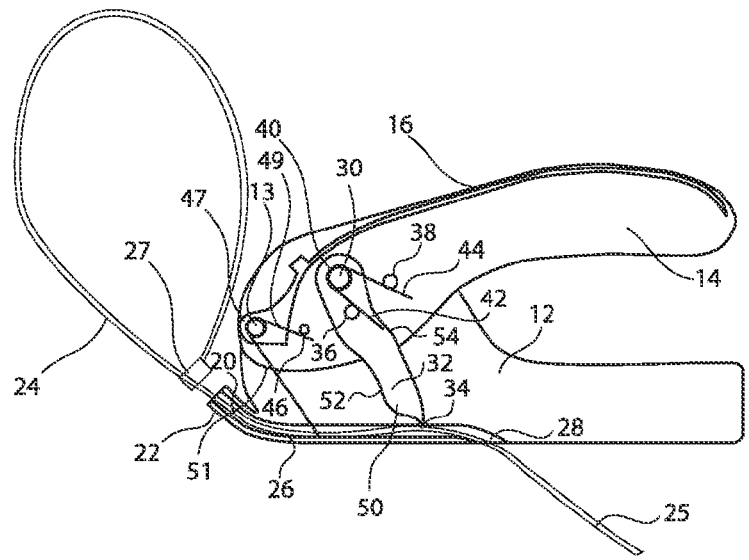
FIG. 4 is a schematic sectional side elevational view similar to the view of FIG. 3, illustrating the thoracic closure device with its handle in a partially depressed position.
Figure 5:
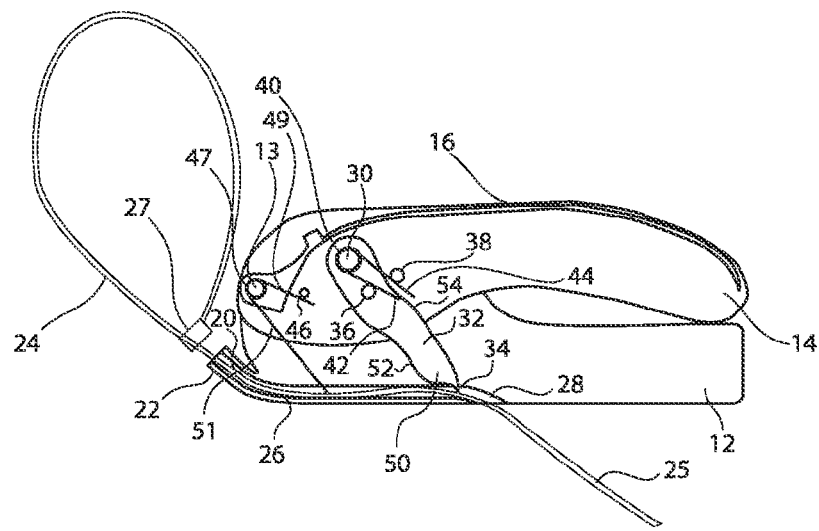
FIG. 5 is a schematic sectional side elevational view similar to the view of FIG. 4, illustrating the thoracic closure device with its handle in a fully depressed position.

FIGS. 4 and 5 illustrate the movement of the handle member 14 and pawl arm 32, as well as the consequent movement of the closure tie 24 along the feed path. As was noted briefly above, the feed path in the illustrated embodiment is a relatively straight path that extends from the first opening 20 to the second opening 28, such that the end of the closure tie 24 moves from the first opening 20 toward the second opening 28. However, the sense of this motion may be reversed in some embodiments. That is, the orientation of the feed path and the particular direction in which the closure tie 24 moves are not critical to the invention.

Additionally, the sense of the movement of the handle member 14 relative to the base member 12 need not be the same in all embodiments. For example, the elastic member 40 and the second elastic member 47 could be arranged so as to bias the handle member 14 toward the base member 12, instead of toward the upward position, and the closure tie 24 could be advanced along the feed path upon movement of the handle member 14 from the depressed position toward the upward position.

In operation, the user would generally insert a closure tie 24 into the first opening 20 and manually advance it a short distance into the base member 12, until the closure tie 24 is far enough along the feed path for the point 34 of the pawl arm 32 to engage the teeth of the closure tie 24. FIGS. 4 and 5 are schematic sectional views similar to the view of FIG. 3 that illustrate the sequence of events when a user pushes down on the handle member 14 with a closure tie 24 in the feed path.

The pawl arm 32 has a cam surface 50 on its trailing edge 52. (The term "trailing edge" is used here with respect to the direction of the feed path and the position shown in FIG. 3; the trailing edge 52 of the pawl arm 32 faces away from the direction in which the closure tie 24 moves, and the leading edge 54 of the pawl arm 32 faces toward the direction.) As the handle member 14 is depressed, the pawl arm 32 is first brought into engagement with the teeth of the closure tie 24, the position shown in FIG. 4. As the motion of the handle member 14 continues, the pawl arm 32 is driven to rotate counterclockwise. The rotation of the pawl arm 32 with its point 34 engaging the teeth of the closure tie 24 moves the closure tie 24 along the feed path.

Ultimately, the rotation of the pawl arm 32 also brings the cam surface 50 on its trailing edge 52 in contact with the closure tie 24, and the interaction of the cam surface 50 and the closure tie 24 causes the point of the pawl arm 34 to disengage and be lifted slightly from the closure tie 24. When the handle member 14 is released, the combination of the resilient force provided by the elastic member 40 and the action of the cam surface 50 returns the pawl arm 32 to a rotational position similar to that of FIG. 3 and forces the point 34 to re-engage with the teeth of the closure tie 24 to hold the closure tie 24 in its new position.

Of course, the user need not complete an entire stroke of the handle member 14 in order to achieve some motion of the closure tie 24, and as long as the user maintains some pressure on the handle member 24 between strokes, the point 34 of the pawl arm 32 will stay in engagement with the closure tie 24 and prevent it from moving along the feed path except toward the second opening 28.

The overall effect of the motion sequence shown in FIGS. 4 and 5 is to produce a unidirectional ratcheting tightening of the closure tie 24. The end of the closure tie 24 is constrained to move from the first opening 20 toward the second opening 28 along the feed path, and is held in place along the feed path as long as the user is exerting some pressure on the handle member 14. Of course, as those of skill in the art will realize, there may be some "slack" or "play" in the mechanism of the device 10, so long as the closure tie 24 does advance along the feed path with each stroke of the handle member 14, and remains in position between strokes. The particular geometry of the device 10, including the stroke length of the handle member 14 and the length, profile and other characteristics of the pawl arm 32 and its cam surface 52, determines the distance that the closure tie 24 will be advanced for each stroke of the handle member 14. Thus, when constructing the device, it is advantageous to balance two competing factors: if it takes too many strokes of the handle member 14 to tighten the closure tie 24, the user may fatigue and the process may become too burdensome; if it takes too few strokes, and the closure tie 24 is moved a relatively great distance on each stroke, then it may not be easy to obtain the required level of tension in the closure tie to effect proper closure. In general, it has been found that an embodiment in which the closure tie 24 is advanced approximately 0.5 inches per stroke is suitable. Of course, the user need not always complete a full stroke if a finer degree of tensioning is desired.

The device 10 and an appropriate closure tie 24 may be used in any procedure in which a fastener is inserted around or through portions of bone or other tissue to bring those portions together by application of tension. However, the following description will focus on the use of the device 10 and closure ties 24 in the closure of a median sternotomy.

Figure 6:
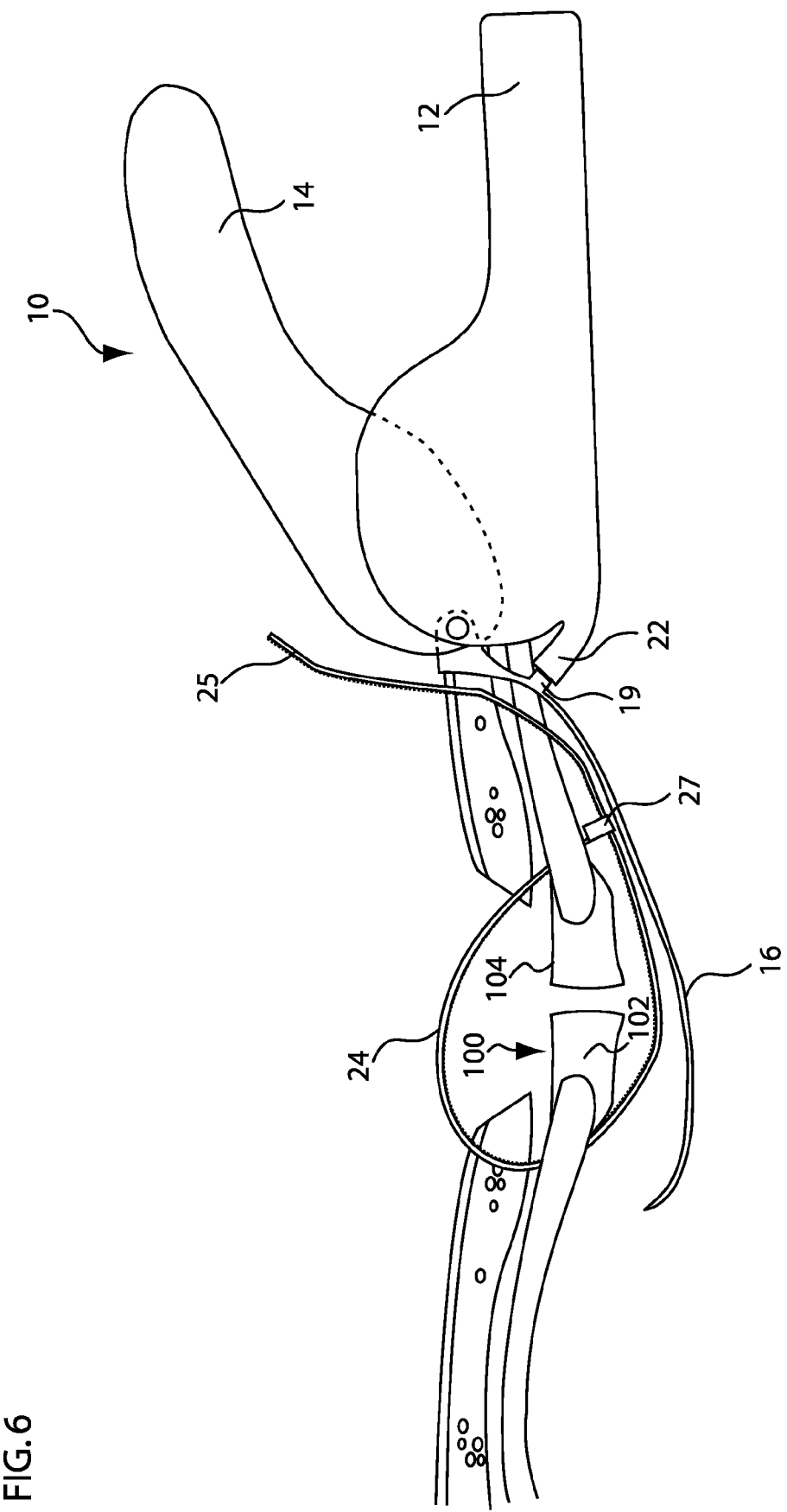
FIG. 6 is a side elevational view illustrating the thoracic closure device in use closing a median sternotomy, with certain thoracic anatomical structures shown schematically in transverse section.

FIG. 6 is a partially sectional side elevational view illustrating the device 10 in use in a first step in the process of closing a median sternotomy. In FIG. 6, the sternum 100 is split into two halves 102, 104. In general, in order to close the median sternotomy properly and bring the two halves 102, 104 together, the user, presumably a surgeon, would install a plurality of closure ties 24 along the length of the sternum 100. It should be understood that the individual closure ties 24 need not necessarily be of the same length or characteristics, so long as the device 10 is capable of engaging them. For example, it may be advantageous to use longer closure ties 24 to encircle the relatively wider manubrium at the top of the sternum 100.

One advantage of the device 10 is that it can be used both to guide the placement of the closure ties 24 and to tension the closure ties 24 once they have been placed.

As shown in FIG. 6, the guide member 16 is extended, inserted into the intercostal spaces between the ribs, and advanced behind the sternum 100 until it emerges from the other side. The guide member 16 thus establishes a path for insertion of a closure tie 24. Depending on the particular configuration of the guide member 16, it may have varying degrees of sharpness and ability to penetrate tissue. A guide member 16 with some penetrative ability may be useful in getting through the tissue in and around the intercostal spaces, but in most embodiments, because the closure ties 24 are adapted to go around the sternum 100, the guide member 16 will not necessarily be equipped to penetrate bone.

A closure tie 24 is then slid down the guide member 16, following its path, until it is in the position shown in FIG. 6. Once the closure tie 24 has been placed beneath the sternum 100, the surgeon withdraws the guide member 16 and returns it to its retracted position within the handle member 14, manually inserts one end 25 of the closure tie 24 into the other end 27 of the closure tie 24, and then inserts the tongue end 25 of the closure tie 24 into the device 10, as described above. Once the tongue end 25 of the closure tie 24

Depending on the surgeon's preference, a number of closure ties 24 may be placed before any are tensioned, or each closure tie 24 may be placed and tensioned in its turn before the next is placed and tensioned. Because the fixed pivot 30 on which the pawl arm 32 is mounted is on the handle member 14, when the handle member 14 is released completely into its upward position, the pawl arm 32 disengages from the closure tie 24 and the closure tie 24 can thus be removed from the device 10. Once a closure tie 24 is placed and tightened, the surgeon may cut off any excess length.

Closure ties 24 with many different shapes, sizes, and tooth configurations may be used with embodiments of the device 10, so long as the device 10 is configured to accept and engage them during the tightening process. In some embodiments, closure ties 24 may also include structure allowing them to cooperate with the guide member 16 during the placement process. For example, a closure tie 24 may be provided with openings, loops, or other structures that would allow it to slide onto the guide member 16, The closure ties 24 may be made of any substantially biocompatible material, and in some embodiments, may be made of a biodegradable, biocompatible plastic. Generally, it is advantageous if the closure ties 24 can withstand approximately 400 N of force for a period of at least 6-8 months, so as to provide adequate strength to close the sternum and to resist the typical physiological forces encountered during daily activities while the bone is healing.

Closure ties 24 made of polyglycolic acid-trimethylene carbonate (PGA-TMC; Smith and Nephew, London, UK), polycaprolactone (PCL; Durect Corporation, Cupertino, Calif., United States), and polylactide (LPLA; Purac, Lincolnshire, Ill., United States) have been found to be suitable for use in embodiments of the present invention, although substantially any biocompatible material may be used in other embodiments.

The device 10 itself would generally be made of a rigid material, such as a metal like aluminum, stainless steel, or titanium, or a hard plastic, such as acrylonitrile-butadiene-styrene (ABS) plastic. It is advantageous if the material of which the device 10 is made can be sterilized by autoclaving or by chemical sterilization processes. In some embodiments, the device 10 may be made to be at least partially disassembled for cleaning purposes.

While the invention has been described with respect to certain embodiments, the embodiments are intended to be exemplary, rather than limiting. Modifications and changes may be made within the scope of the invention, which is defined by the claims.

What is claimed is:

1. A thoracic closure device, comprising:
   a base member having a first end, a second end, an internal surface, and a feed path defined between the first and second ends along the internal surface, the feed path terminating in an opening at one or both of the first and second ends;
   a handle member having a first end and a second end, the handle member being mounted on the base member for rotation about a first generally horizontally-extending axis of rotation between (1) a first position, in which the second end of the handle member is angularly displaced from the base member, and (2) a second position in which the second end of the handle member is proximate to the base member;
   an elongate pawl arm having
      a first end mounted for rotation about a second generally horizontally-extending axis of rotation defined by a post within the handle member and spaced from the first axis of rotation on which the handle is mounted,
      a second end opposite the first end,
      an engaging structure disposed at the second end of the pawl arm, and
      a cam surface on a trailing side of the pawl arm, the cam surface extending between the first and second ends of the pawl arm;
   an elastic member mounted within the thoracic closure device, the elastic member being arranged to bear between the handle member and the pawl arm to place the handle member in a driving relationship with respect to the pawl arm such that (1) the pawl arm is biased toward the internal surface of the base member and, if a toothed closure tie is in the feed path, the engaging structure of the pawl arm engages the teeth of the closure tie, and (2) as the handle member is moved between the first and second positions, the pawl arm is driven to rotate in such a way as to advance the closure tie unidirectionally along the feed path before the elastic member resiliently returns the pawl arm to a position in which the engaging structure is in engagement with the teeth of the toothed closure tie; and
   a stop post on the handle member, the stop post being constructed and arranged to block the rotation of the pawl arm in order to prevent the pawl arm from engaging the closure tie prior to a defined point in the feed path.

2. The thoracic closure device of claim 1, wherein the opening is provided at the first end of the base member, and a second opening is provided, spaced from the first opening.

3. The thoracic closure device of claim 2, wherein the feed path is oriented such that the closure tie is drawn into the opening at the first end of the base member and fed toward the second opening of the base member.

4. The thoracic closure device of claim 3, wherein the trailing edge of the pawl arm faces the opening at the first end of the base member.

5. The thoracic closure device of claim 4, wherein the device is constructed such that as the handle member is moved toward the second position, the pawl arm is driven to rotate with its engaging structure in engagement with one or more teeth of the closure tie in such a way as to advance the closure tie along the feed path toward the second opening of the base member before the elastic member resiliently returns the pawl arm to a position in which the engaging structure is in engagement with the teeth of the toothed closure tie.

6. The thoracic closure device of claim 1, wherein the second generally horizontally-extending axis of rotation is defined by a generally horizontally-oriented post in the handle member.

7. The thoracic closure device of claim 6, wherein the elastic member is a torsional spring mounted on the generally horizontally-oriented post in the handle member, the torsional spring having first and second legs, the first leg of the torsional spring bearing against a generally horizontally-extending post on the pawl arm, and the second leg of the torsional spring bearing against a generally horizontally-extending post on the interior of the handle member.

8. The thoracic closure device of claim 1, wherein when the handle member is in the first position, the pawl arm does not engage the closure tie in the feed path.

9. A thoracic closure device, comprising:
   a base member having a first end, a second end, an internal surface, and a feed path defined between the first and second ends along the internal surface, the feed path terminating in an opening at one or both of the first and second ends;
   a handle member having a first end and a second end, the handle member being mounted on the base member for rotation about a first generally horizontally-extending axis of rotation between (1) a first position, in which the second end of the handle member is angularly displaced from the base member, and (2) a second position in which the second end of the handle member is proximate to the base member;
   an elongate pawl arm having
      a first end mounted for rotation about a second generally horizontally-extending axis of rotation defined by a post within the handle member and spaced from the first axis of rotation on which the handle is mounted,
      a second end opposite the first end,
      an engaging structure disposed at the second end of the pawl arm, and
      a cam surface on a trailing side of the pawl arm, the cam surface extending between the first and second ends of the pawl arm;
   an elastic member mounted within the thoracic closure device, the elastic member being arranged to bear between the handle member and the pawl arm to place the handle member in a driving relationship with respect to the pawl arm such that (1) the pawl arm is biased toward the internal surface of the base member and, if a toothed closure tie is in the feed path, the engaging structure of the pawl arm engages the teeth of the closure tie, and (2) as the handle member is moved between the first and second positions, the pawl arm is driven to rotate in such a way as to cause the pawl arm to advance the closure tie unidirectionally along the feed path before the elastic member resiliently returns the pawl arm to a position in which the engaging structure is in engagement with the teeth of the toothed closure tie; and
   an elongate guide member mounted on the handle member for rotation about a third generally horizontally-extending axis of rotation between extended positions, in which an end of the elongate guide member extends outwardly of the thoracic closure device and retracted positions, in which the elongate guide member is substantially contained within the handle member.

10. The thoracic closure device of claim 9, wherein a first opening is provided at the first end of the base member, and a second opening is provided in the base member, spaced from the first opening.

11. The thoracic closure device of claim 10, wherein the feed path is oriented such that the closure tie is drawn into the opening at the first end of the base member and fed toward the second opening of the base member.

12. The thoracic closure device of claim 11, wherein the trailing edge of the pawl arm faces the opening at the first end of the base member.

13. The thoracic closure device of claim 12, wherein the cam surface on the trailing edge of the pawl arm moves the engaging structure out of engagement with the closure tie as the pawl arm rotates toward the second opening.

14. The thoracic closure device of claim 9, wherein the second generally horizontally-extending axis of rotation is defined by a generally horizontally-oriented post in the handle member.

15. The thoracic closure device of claim 14, wherein the elastic member is a torsional spring mounted on the generally horizontally-oriented post in the handle member, the torsional spring having first and second legs, the first leg of the torsional spring bearing against a generally horizontally-extending post on the pawl arm, and the second leg of the torsional spring bearing against a generally horizontally-extending post on the interior of the handle member.

16. The thoracic closure device of claim 9, further comprising a stop post on the base member, the stop post being constructed and arranged to block the rotation of the pawl arm in order to prevent the pawl arm from engaging the closure tie prior to a defined point in the feed path.

17. The thoracic closure device of claim 9, wherein the handle member further comprises a recess constructed and arranged to contain the guide member.

18. The thoracic closure device of claim 17, wherein the third generally horizontally-extending axis of rotation is defined by pin mounted in the recess of the handle member.

19. A thoracic closure device, comprising:
   a base member having a first end, a second end, a bottom, and a feed path defined between the first and second ends along the bottom, the feed path originating at a first opening in the first end and terminating at a second opening in the bottom;
   a handle member having a first end and a second end, the handle member being mounted on the base member for rotation about a first generally horizontally-extending axis of rotation between (1) a first position, in which the second end of the handle member is angularly displaced from the base member, and (2) a second position in which the second end of the handle member is proximate to the base member;
   an elongate pawl arm having
      a first end mounted for rotation about a second generally horizontally-extending axis of rotation defined by a post in the handle member,
      a second end opposite the first end,
      an engaging structure disposed at the second end of the pawl arm, and
      a cam surface on a trailing side of the pawl arm, the cam surface extending between the first and second ends of the pawl arm; and
   an elastic member mounted within the handle member, the elastic member being arranged to bear between the handle member and the pawl arm to place the handle member in a driving relationship with respect to the pawl arm such that (1) the pawl arm is biased toward the bottom of the base member and, if a toothed closure tie is in the feed path, the engaging structure of the pawl arm engages the teeth of the closure tie, and (2) as the handle member is moved from the first position toward the second position, the pawl arm is driven to rotate in such a way as to advance the closure tie unidirectionally along the feed path by engagement of the engaging structure and the closure tie before the cam surface moves the engaging structure out of engagement with the closure tie and the elastic member resiliently returns the pawl arm to a position in which the engaging structure is in engagement with the teeth of the toothed closure tie.

* * * * *